US006932782B2

(12) United States Patent  
Ferraioli

(10) Patent No.: US 6,932,782 B2
(45) Date of Patent: Aug. 23, 2005

(54) FLEXIBLE SPLINT

(76) Inventor: Michael P. Ferraioli, 102 E. 7th St., New York, NY (US) 10009

(*) Notice: Subject to any disclaimer, the term of this patent is extended or adjusted under 35 U.S.C. 154(b) by 0 days.

(21) Appl. No.: 10/260,366

(22) Filed: Sep. 30, 2002

(65) Prior Publication Data

US 2004/0002673 A1 Jan. 1, 2004

Related U.S. Application Data

(60) Provisional application No. 60/392,825, filed on Jul. 1, 2002.

(51) Int. Cl.[7] .................................................. A61F 5/00
(52) U.S. Cl. ............................ 602/22; 602/30; 128/880
(58) Field of Search ............................... 60/5–7, 20–22, 60/30, 63; 128/878–880, 893, 894

(56) References Cited

U.S. PATENT DOCUMENTS

| | | | | |
|---|---|---|---|---|
| 1,358,272 A | * | 11/1920 | Wilson | 128/894 |
| 1,823,904 A | * | 9/1931 | Kaiser | 128/880 |
| 2,120,465 A | * | 6/1938 | Hartley | 128/894 |
| 2,423,538 A | * | 7/1947 | Whiteford | 128/894 |
| 2,528,456 A | * | 10/1950 | Stevenson | 602/22 |
| 2,548,378 A | * | 4/1951 | Kleinfeld | 602/22 |
| 2,918,059 A | * | 12/1959 | Levitt | 602/30 |
| 2,923,292 A | * | 2/1960 | Dorr | 128/894 |
| 3,039,460 A | * | 6/1962 | Chandler | 602/22 |
| 3,088,461 A | * | 5/1963 | Levitt | 128/894 |
| 3,170,460 A | * | 2/1965 | Stilson | 602/22 |
| 3,209,750 A | * | 10/1965 | Levitt | 128/894 |
| 3,244,171 A | * | 4/1966 | Neu | 128/894 |
| 3,482,569 A | * | 12/1969 | Raffaelli | 128/894 |
| 4,103,682 A | * | 8/1978 | Franzl | 602/22 |
| 4,270,528 A | * | 6/1981 | Hanson | 602/22 |
| 4,665,907 A | * | 5/1987 | Leverette | 128/880 |
| 4,770,166 A | * | 9/1988 | Garris | 602/22 |
| 5,665,060 A | * | 9/1997 | Fabricant | 602/30 |
| 6,110,136 A | * | 8/2000 | Belkin | 602/22 |

OTHER PUBLICATIONS

SU 1195998 A.*
FR 2578–740–A.*
EP–183– 021–A.*

* cited by examiner

Primary Examiner—Michael A. Brown
Assistant Examiner—Huong Q. Pham
(74) Attorney, Agent, or Firm—John W. LaBatt; Hoffman, Warnick, & D'Alessandro LLC

(57) ABSTRACT

A device for limiting movement of a joint. Once prepared, the device includes two tubular openings for encircling phalanxes on either side of the joint. The tubular sides are attached by a portion of the device that can cover either the top portion of the joint or the underside of the joint. This configuration allows an individual to flex the joint in a limited manner.

20 Claims, 6 Drawing Sheets

FLEXIBLE SPLINT

REFERENCE TO PRIOR APPLICATION

The current application claims priority to provisional application Ser. No. 60/392,825, filed on Jul. 1, 2002 and incorporated herein by reference.

BACKGROUND OF THE INVENTION

1. Technical Field

The invention generally relates to devices for restricting the movement of joints. In particular, the invention provides a device for limiting the movement of a joint, while allowing the joint to retain sufficient mobility for functioning, i.e., gripping with a hand.

2. Background Art

Joint stiffening or locking can occur due to several different causes, for example, arthritis, trauma, etc. Joints of fingers, for example, can frequently become stiffened or locked. Several devices exist for the aid and therapy of fingers. Generally, these devices completely immobilize a finger, thereby preventing all movement. While immobilization prevents the joint from locking, the finger cannot be used for various hand functions, for example, gripping. Further, the immobilization does not provide any therapeutic assistance in repairing the joint.

In addition, preexisting devices are provided in a limited number of sizes to conform to common finger sizes. Manufacturing of various device sizes adds complication and expense to the manufacturing process. Further, retailers and physicians are then required to stock the various sizes. In some instances, an individual's finger may not conform to any of the readily available device sizes, thereby limiting the effectiveness of the device.

Some devices also include only a small surface area in contact with the finger. Due to the small surface area, a relatively high amount of pressure is applied at the limited contact areas of the finger causing discomfort for the user. Further, the small contact areas may cause the device to become unstable and slip when the joint is moved.

As a result, there exists a need for a flexible splint that allows a joint to maintain some movement, thereby allowing the finger to remain functional. Additionally, there exists a need for a flexible splint device that is adjustable to conform to any finger size. Further, a need exists for a flexible splint device that provides increased comfort and stability when in use.

SUMMARY OF THE INVENTION

The current invention provides a flexible splint for providing limited movement to a joint. The flexible splint includes a connected pair of tubular sides that encircle the phalanxes on either side of the joint, and a connector that covers a portion of the joint thereby limiting its movement.

A first aspect of the invention provides a device for limiting movement of a joint, comprising: an elongate member having: a first end; a second end, opposite the first end; and an elongate opening formed between the first end and the second end; wherein the first end attaches to the second end, forming a connected pair of tubular sides between which the joint is positioned.

A second aspect of the invention provides a device for limiting movement of a joint, comprising: a first tubular side; a second tubular side substantially parallel to the first tubular side; a connector attaching a portion of the first tubular side to a portion of the second tubular side; and wherein the joint is positioned between the first tubular side and the second tubular side.

A third aspect of the invention provides a device for limiting movement of a joint, comprising: means for encircling a phalanx on a first side of the joint; means for encircling a phalanx on a second side of the joint; and means for attaching the means for encircling the first side to the means for encircling the second side.

The illustrative aspects of the present invention are designed to solve the problems herein described and other problems not discussed, which are discoverable by a skilled artisan.

BRIEF DESCRIPTION OF THE DRAWINGS

These and other features of this invention will be more readily understood from the following detailed description of the various aspects of the invention taken in conjunction with the accompanying drawings in which.

It is noted that the drawings of the invention are not to scale. The drawings are intended to depict only typical aspects of the invention, and therefore should not be considered as limiting the scope of the invention. In the drawings, like numbering represents like elements between the drawings.

DETAILED DESCRIPTION OF THE INVENTION

The current invention provides a device for limiting the movement of a joint of a finger. The device can be used to cover either the top portion of the joint or the underside of the joint, while encircling the phalanxes (phalanges) on either side of the joint. In this manner, the joint is allowed to flex, but cannot flex over its entire range of motion.

Figure 1:
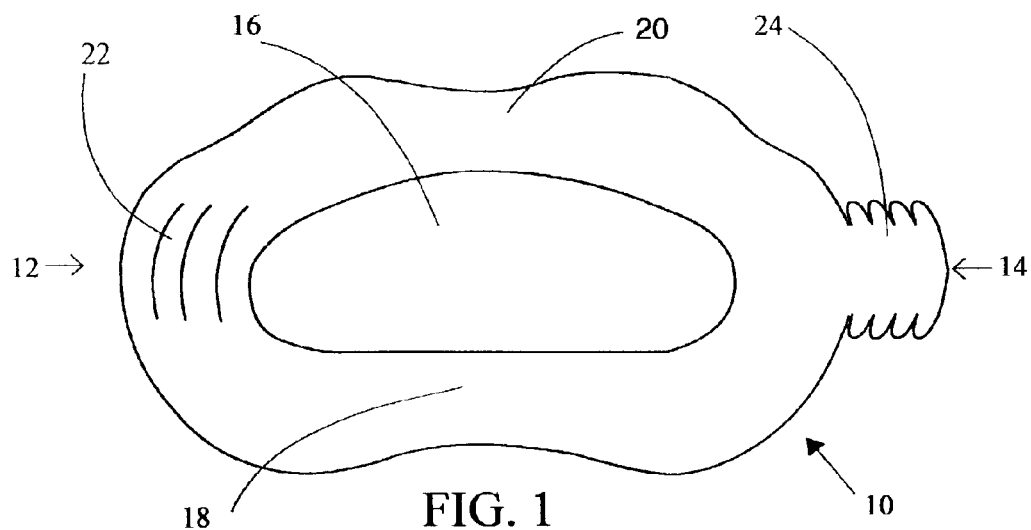
FIG. 1 shows a view of a device according to one aspect of the invention.

Turning to the Figures, FIG. 1 shows a view of a device 10 according to one aspect of the invention. Device 10 is shown having a first end 12 and a second end 14, located opposite first end 12. An elongate opening 16 is shown formed between the first end and the second end, forming a first side 18 and a second side 20. First end 12 is configured to be attached to second end 14. First end 12 can be removably or permanently attached to second end 14 using any means now known or later developed.

Figures 2, 3, 4:
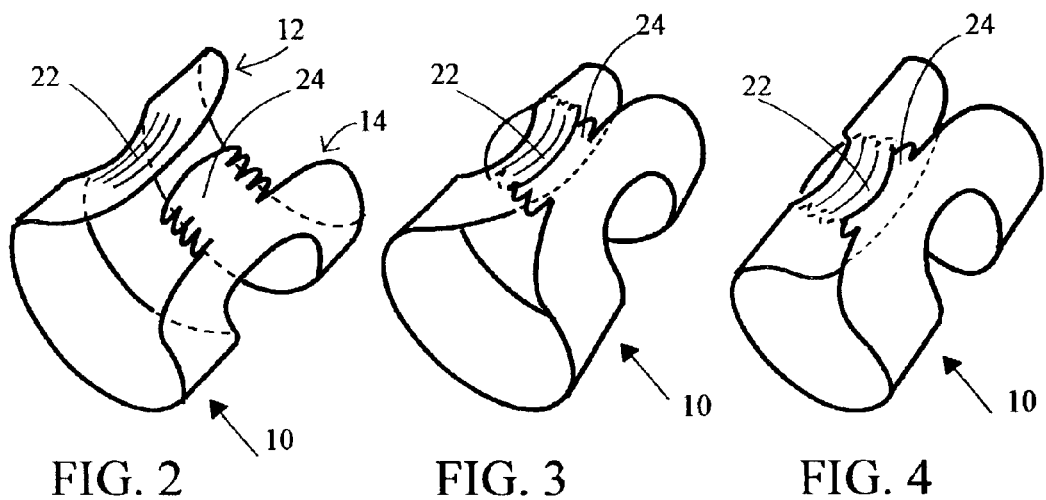
FIG. 2 shows a first step of forming the device of FIG. 1 for positioning on a finger.
FIG. 3 shows a second step of forming the device of FIG. 1 for positioning on a finger.
FIG. 4 shows the device of FIG. 1 formed for positioning on a finger.
Figure 5:
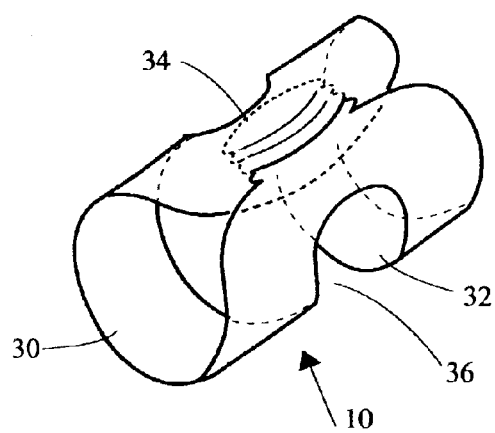
FIG. 5 shows a perspective view of the device of FIG. 1.
Figure 6:
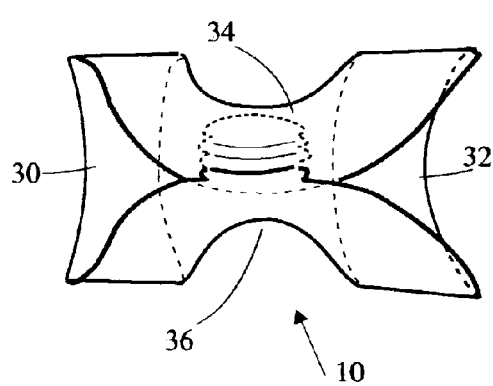
FIG. 6 shows a top view of the device of FIG. 1.
Figure 7:
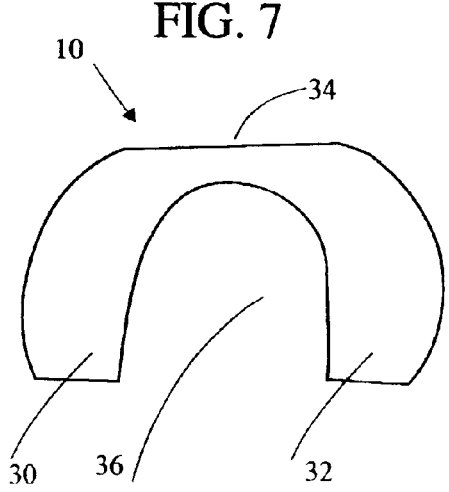
FIG. 7 shows a side view of the device of FIG. 1.
Figure 8:
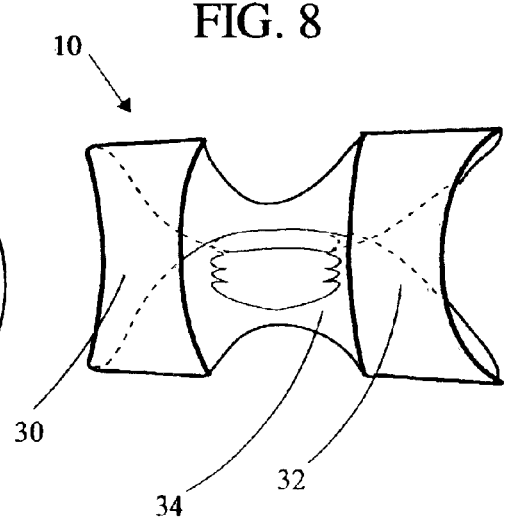
FIG. 8 shows a bottom view of the device of FIG. 1.

For example, first end 12 can include one or more slots 22 and second end 14 can include one or more tabs 24. As shown in FIGS. 2–4, device 10 can be curled so that first end 12 and second end 14 are brought together. This allows one of tabs 24 to be inserted and secured within one of slots 22. Alternatively, first end 12 can be attached to second end 14 using a hook and latch fastener, a snap, a button, stitching, tape, glue, etc. First end 12 can be attached to second end 14 around a joint to help ensure a proper and snug fit. However, first end 12 can also be attached to second end 14 and device 10 can be inserted around a finger and aligned with the desired joint.

As shown in FIG. 1, device 10 includes three slots 22 on first end 12, and four tabs 24 on second end 14. This illustrative arrangement allows for the accommodation of twelve different sizes. It is understood that this is only illustrative, and more or less slots 22 and tabs 24 can be included. In addition, it is understood that the use of slots 22 and tabs 24 to accommodate various sizes is also only illustrative of the possible methods of providing adjustable sizing. Further, device 10 can be manufactured in one or more sizes with or without the ability to adjust the size. Available sizing options for device 10 can be made to conform to the various ring sizes of individuals.

Once first end 12 is attached to second end 14, device 10 comprises a connected pair of tubular sides between which a joint can be positioned. FIGS. 5–8 show a perspective, top, side, and bottom view of device 10 after having been formed to function as a flexible splint. As can be seen, device 10 includes a first tubular side 30, and a second tubular side 32 attached by a connector 34. A cut out area 36 is formed below connector 34 and between tubular sides 30, 32. As clearly shown in FIG. 8, tubular side 30 is smaller than tubular side 32 to conform to the natural shape of a finger. Further, tubular sides 30, 32 form tapered openings to further conform to the finger. Alternatively, tubular sides 30, 32 can form non-tapered openings of substantially the same size or different sizes. For example, when desired for use on the joint on the thumb, non-tapered openings of substantially the same size may be desired. However, additional or reduced tapering for tubular sides 30, 32 can also be obtained through the selected method of attaching first end 12 with second end 14. For example, slots 22 and tabs 24 shown in FIG. 1 can be configured so that sufficient lateral movement is retained to provide for a variable amount of tapering of tubular sides 30, 32 to accommodate the thumb and various finger shapes.

Figure 9:
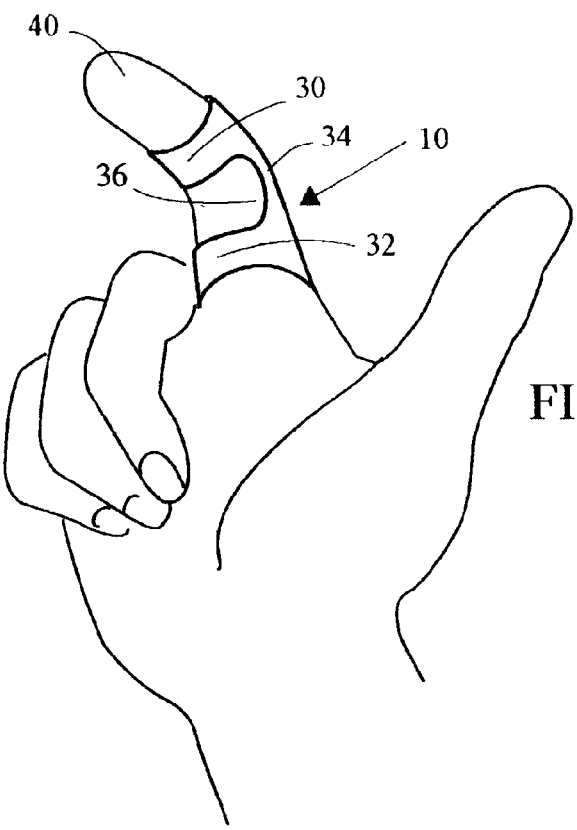
FIG. 9 shows a palm-side view of a device according to the invention positioned on a finger.
Figure 10:
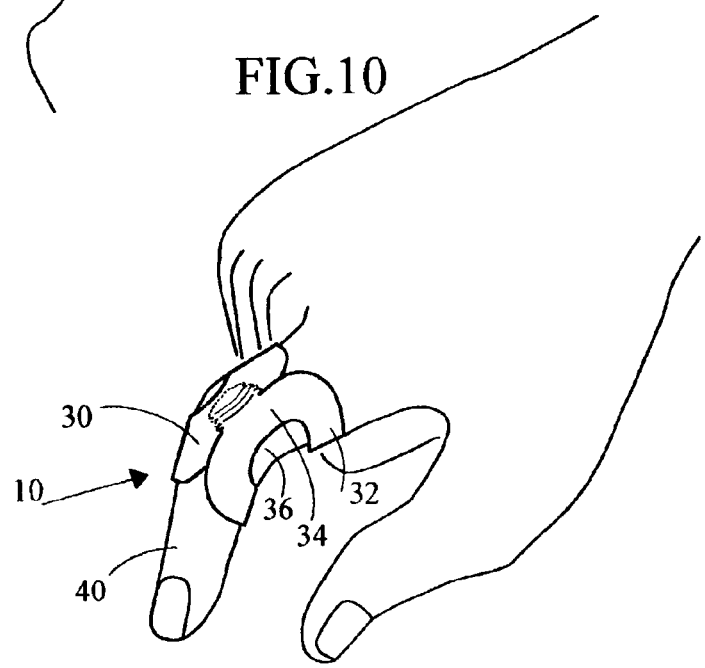
FIG. 10 shows a view from the back of a hand having a device according to the invention positioned on a finger.
Figure 11:
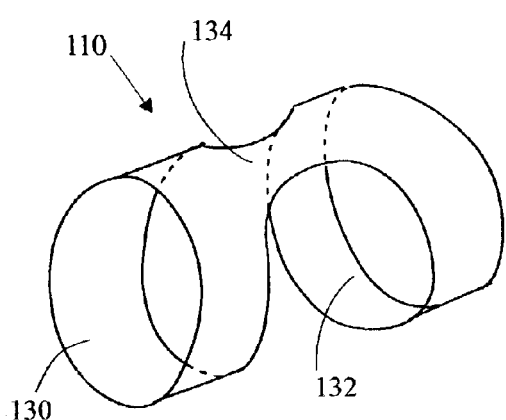
FIG. 11 shows a perspective view of an alternative device according to another aspect of the invention.
Figure 12:
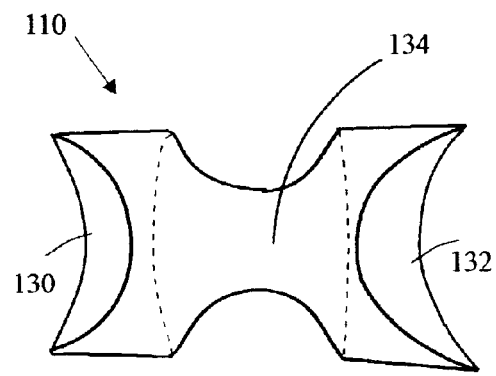
FIG. 12 shows a top view of the device of FIG. 11.
Figure 13:
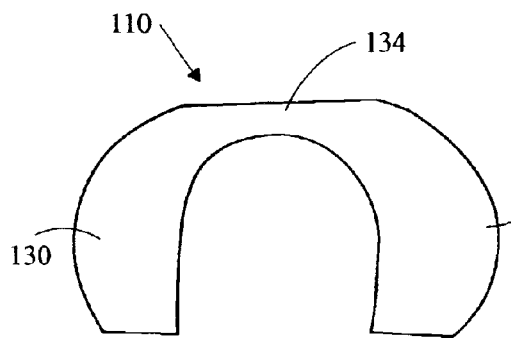
FIG. 13 shows a side view of the device of FIG. 11.
Figure 14:
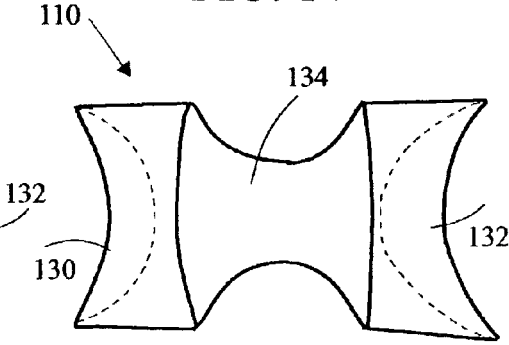
FIG. 14 shows a bottom view of the device of FIG. 11.

FIGS. 9 and 10 show alternative perspective views of device 10 positioned on a finger 40. As shown, tubular side 32 is located on the palm-side of a joint, while tubular side 30 is located on the opposite side of the joint. Each tubular side is positioned to encircle a phalanx (i.e., bone) on either side of a joint. Because of the respective sizes and tapering of tubular sides 30, 32, both sides conform to the size and shape of finger 40. Connector 34 is located so that it covers the top of the joint, thereby aligning cut out area 36 with the bottom of the joint. With this configuration, an elongated surface area of device 10 covers the top of the joint thereby preventing movement. This surface area acts to distribute the pressure applied when a joint is moved, and also provides stability so that the location of device 10 does not move relative to the joint.

Figure 15:
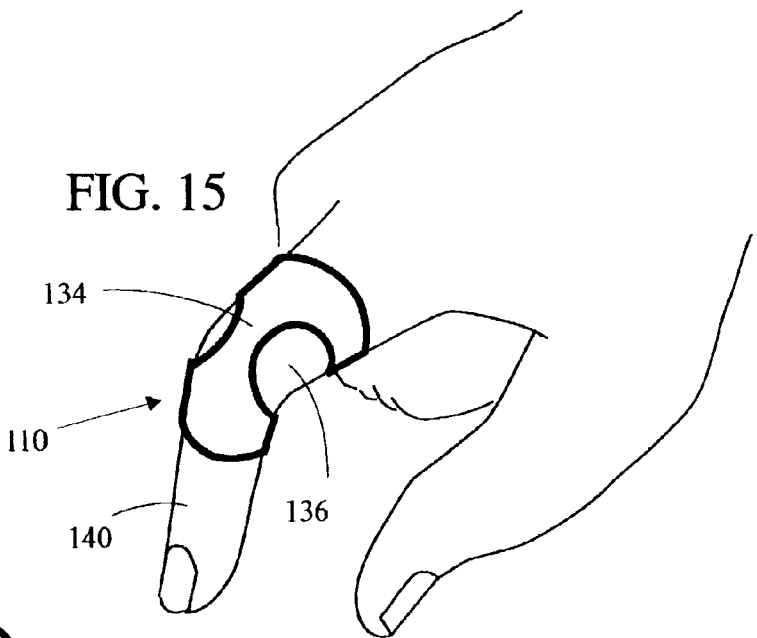
FIG. 15 shows a perspective view of the device of FIG. 11 positioned on a finger.
Figure 16:
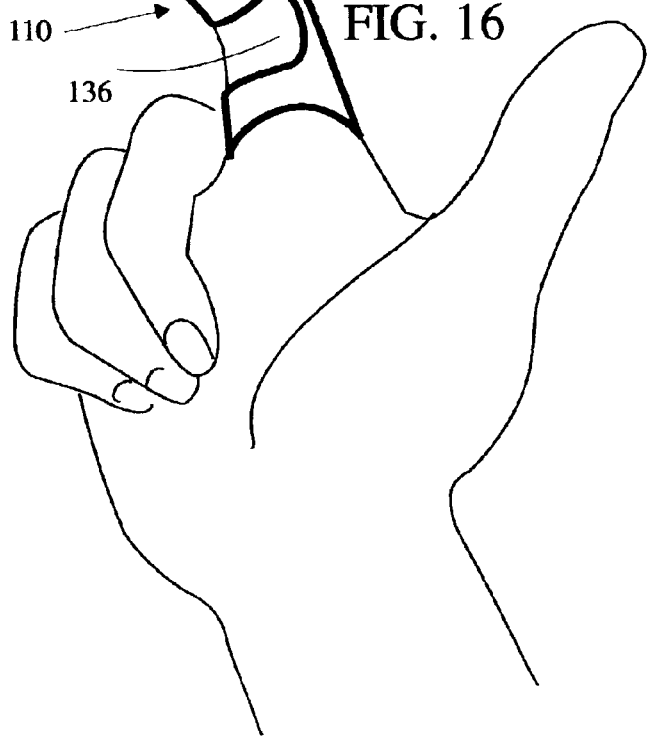
FIG. 16 shows a palm-side view of the device of FIG. 11 positioned on a finger.

The flexible splint can also be manufactured as a single, preformed molded unit. For example, FIGS. 11–14 show a perspective, top, side, and bottom view, respectively, of a device 110 comprising a first tubular side 130, and a second tubular side 132 attached by a connector 134 that has been manufactured as a preformed molded unit. As shown, device 110 can be molded in a form similar to device 10 after having the ends attached as depicted in FIGS. 5–8. Additionally, FIGS. 15 and 16 show device 110 positioned on a finger 140. Connector 134 is shown substantially aligned over the joint, thereby aligning cut out area 136 with the bottom of the joint.

Figure 17:
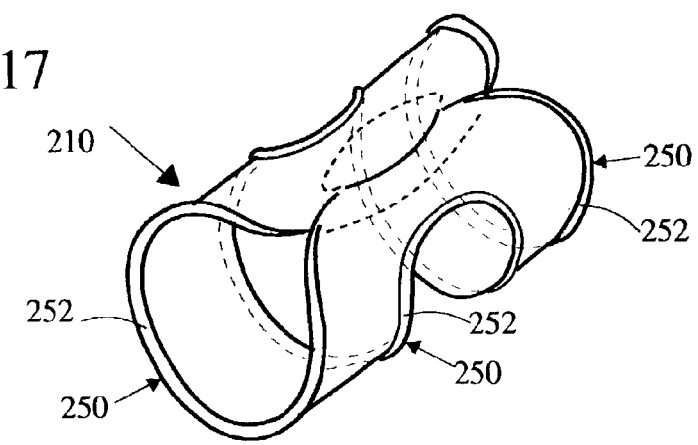
FIG. 17 shows a perspective view of a device having exposed edges that include flanges.
Figure 18:
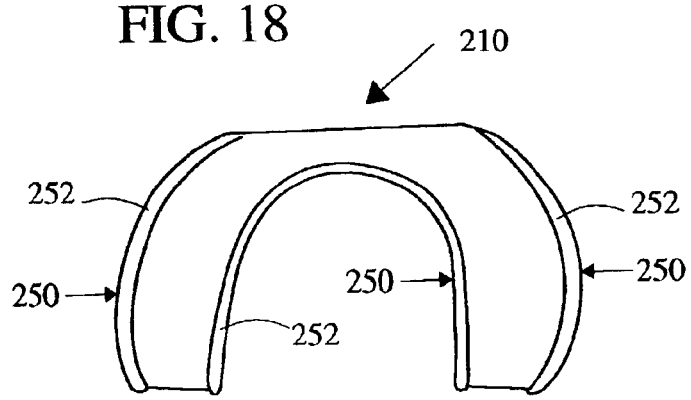
FIG. 18 shows a side view of the device of FIG. 17.

The edges of the device and/or interior of the device can be configured to further enhance the comfort of the device when positioned on an individual's finger. For example, the inner and/or outer edges of the device can be rounded. Additionally, FIGS. 17 and 18 show a perspective and side view, respectively, of a device 210 having edges 250 that include flanges 252 for providing additional rounding of edges 250. Flanges 252 are configured to protrude away from the finger on which device 210 is positioned. As shown, the thickness of flanges 252 can be adjusted according to the amount of flexibility that is desired for a particular portion of device 210. E.g., the surface area of flange 252 can be reduced where flexibility is desired, and increased where flexibility is not required.

Figure 19:
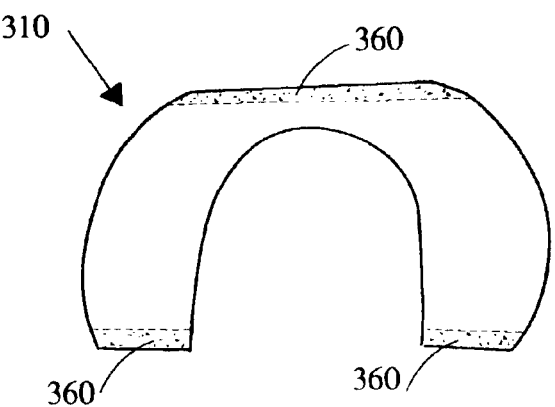
FIG. 19 shows a side view of a device having softening material attached to portions of the interior surfaces.

FIG. 19 shows a device 310 in which portions of the interior surfaces that contact the finger have a softening material 360 attached thereto for cushioning the contact of device 310 with a finger. Softening material 360 can comprise any type of material suitable for cushioning the contact between device 310 and a finger, for example, a foam material, a cotton fabric, a soft plastic, etc. Softening material 360 can be permanently or temporarily attached to device 310 by glue or tape, for example, or any means now known or later developed.

While two illustrative methods of manufacturing the device of the current invention are shown and discussed, it is understood that any valid manufacturing of the device is possible according to the current invention. For example, the connector and tubular sides can be formed separately, and subsequently be permanently or temporarily attached using any system now known or later developed. Additionally, each tubular side can be made to be individually adjustable by being individually formed, for example, by a strap attached using a hook and latch fastener.

The device of the current invention can comprise any material possessing sufficient strength and flexibility for limiting the motion of a joint. For example, the device can comprise a hardened polystyrene plastic of a width such that sufficient flexibility is retained to attach the first end to the second end. In this case, the edges of the device may comprise a non-hardened polystyrene plastic or similar material to increase user comfort. Alternatively, the device can comprise polypropylene, rubber, latex, vinyl, leather, cotton fabric, stretch fabric, etc.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to a person skilled in the art are intended to be included within the scope of the invention as defined by the accompanying claims.

What is claimed is:

1. A device for limiting movement of a joint, comprising:
   a unitary elongate member having, in a planar first position:
   a first end having a first attachment means;
   a second end, opposite the first end, and having a second attachment means; and
   an elongate opening formed between the first end, the second end, a first side, and
   a second side, wherein the first and second attachment means are centrally located between the first side and the second side;
   wherein the first end attaches to the second end using the first and second attachment means, forming a second position of the elongate member having:
   a first tubular member formed by the first side;
   a second tubular member formed by the second side; and
   a connector formed by the attachment of the first end to the second end, the connector attaching a portion of the first tubular member to a portion of the second tubular member, and wherein the first and second attachment means are centrally located on the connector between the first tubular member and the second tubular member.

2. The device of claim 1, wherein the first attachment means comprises at least one tab attached to the first end; and wherein the second attachment means comprises at least one slot inserted on the second end.

3. The device of claim 1, wherein the first and second attachment means comprise at least one of the following hook and latch fastener, a snap, a button, and tape.

4. The device of claim 1, comprising one of the following a polystyrene plastic, polypropylene, rubber, latex, vinyl, leather, cotton fabric, and stretch fabric.

5. The device of claim 1, wherein the first end adjustably attaches to the second end.

6. The device of claim 1, wherein a first tubular member is smaller than a second tubular member.

7. The device of claim 1, wherein each tubular member forms a tapered opening.

8. The device of claim 1, wherein at least one edge of the device is rounded.

9. The device of claim 8, wherein at least one edge of the device includes a flange configured to protrude away from the joint.

10. The device of claim 1, further comprising a softening material attached to an interior portion of the device.

11. The device of claim 10, wherein the softening material comprises one of the following a foam material, and a cotton fabric.

12. A device for limiting movement of a joint, comprising:
    a first tubular member;
    a second tubular member substantially parallel to the first tubular member;
    a connector attaching a portion of the first tubular member to a portion of the second tubular member, wherein the connector comprises:
    a first end having a first attachment means centrally located between the first and second tubular members; and
    a second end having a second attachment means centrally located between the first and second tubular members and removably attached to the first attachment means, an elongated opening formed between the first tubular member, the second tubular member, the first end, and the second end, wherein the first and second attachment means allow the connector to retain sufficient lateral movement to provide a variable amount of tapering of at least one of: the first tubular member and the second tubular member; and
    wherein the joint is positioned between the first tubular member and the second tubular member.

13. The device of claim 12, wherein the first tubular member and the second tubular member form tapered openings.

14. The device of claim 12, wherein the first tubular member is smaller then the second tubular member.

15. The device of claim 12, wherein each edge of each tubular member is rounded.

16. The device of claim 12, further comprising a softening material attached to an interior portion of the device.

17. A device for limiting movement of a joint, the device comprising:
    a unitary elongate member having, in a planar first position:
    a first end having a curved slot;
    an opposing second end having a tab;
    a first side and art opposing second side; and
    an elongate aperture formed between the first end, the second end, the first side, and the second side;
    wherein the first end attaches to the second end using the tab and the curved slot, forming a second position of the elongate member having:
    a first tubular side formed by the first side; and
    a second tubular side formed by the second side; wherein the joint is positioned between the first tubular side and the second tubular side, and wherein each tubular side retains a variable amount of tapering.

18. The device of claim 17, wherein the first end includes a plurality of curved slots.

19. The device of claim 17, wherein the second end includes a plurality of tabs.

20. The device of claim 12, wherein the first centrally located attachment means comprises at least one tab attached to the first end; and wherein the second centrally located attachment means comprises at least one slot inserted on the second end.

* * * * *

UNITED STATES PATENT AND TRADEMARK OFFICE
CERTIFICATE OF CORRECTION

PATENT NO. : 6,932,782 B2
DATED : August 23, 2005
INVENTOR(S) : Michael P. Ferraioli It is certified that error appears in the above-identified patent and that said Letters Patent is hereby corrected as shown below:

Column 1,
Line 5, please insert -- co-pending -- before the word "provisional".

Column 6,
Line 26, please take out the word "then" and insert -- than --.

Signed and Sealed this

Sixth Day of December, 2005

JON W. DUDAS
*Director of the United States Patent and Trademark Office*